(12) United States Patent
Slater

(10) Patent No.: US 6,873,409 B1
(45) Date of Patent: Mar. 29, 2005

(54) OPTICAL PROBE WITH SAMPLING WINDOW CLEANING CONFIGURATION

(75) Inventor: Joseph B. Slater, Dexter, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 0 days.

(21) Appl. No.: 09/441,683

(22) Filed: Nov. 16, 1999

Related U.S. Application Data

(60) Provisional application No. 60/108,720, filed on Nov. 17, 1998.

(51) Int. Cl.[7] .................................................. G01J 3/44
(52) U.S. Cl. ...................................................... 356/301
(58) Field of Search ........................... 356/301; 359/509

(56) References Cited

U.S. PATENT DOCUMENTS

| | | | |
|---|---|---|---|
| 4,281,646 A | * 8/1981 | Kinoshita | ................. 134/104.1 |
| 4,836,689 A | * 6/1989 | O'Brien et al. | ............. 359/509 |
| 4,976,871 A | * 12/1990 | Banks et al. | ................. 210/709 |
| 5,261,410 A | * 11/1993 | Alfano et al. | .......... 250/339.12 |
| 5,333,609 A | * 8/1994 | Bedingham et al. | ........ 600/339 |
| 5,575,756 A | * 11/1996 | Karasawa et al. | .......... 600/121 |
| 5,630,795 A | * 5/1997 | Kuramoto et al. | .......... 600/153 |
| 5,845,646 A | * 12/1998 | Lemelson | .................... 128/899 |

* cited by examiner

Primary Examiner—Zandra V. Smith
(74) Attorney, Agent, or Firm—Gifford, Krass, Groh, Sprinkle, Anderson & Citkowski, PC

(57) ABSTRACT

A self-cleaning optical probe includes a probe body having a window with a surface oriented toward a sample under investigation. A sampling beam carrying wavelengths representative of the sample passes into the probe body through the window for analysis. A conduit, preferably forming part of the probe body, is used to carry a fluid to the surface of the window oriented toward the sample, and a partition proximate to the window is used to direct the fluid across the window as a laminar flow. The partition further includes an aperture through which the sampling wavelengths pass. This partition also permits a portion of the fluid to pass though the aperture to ensure that the sample under investigation does not reach the window. The fluid may be a liquid or gas, and is preferably a solvent to maximize window cleaning. Although the fluid may be discharged without entering into the environment being sampled, the fluid may also be discharged into the sample, depending upon the application, volume of the respective fluid/sample flows, and other such factors.

11 Claims, 1 Drawing Sheet

US 6,873,409 B1

OPTICAL PROBE WITH SAMPLING WINDOW CLEANING CONFIGURATION

REFERENCE TO RELATED APPLICATION

This application claims priority from U.S. provisional application Ser. No. 60/108,720, filed Nov. 17, 1998, the entire contents of which are incorporated herein by reference.

FIELD OF THE INVENTION

This invention relates generally to optical probes and, in particular, to a probe having a self-cleaning capability for use in on-line process control and other applications.

BACKGROUND OF THE INVENTION

Optical probes such as those used for Raman detection are increasingly being employed in on-line process-control applications. In a typical configuration, this requires that at least the sampling optic be immersed directly into a process stream. In many cases, the process stream contains materials which tend to coat the optic, thereby reducing or completely eliminating the ability to collect data.

Many solutions have been tried to compensate for, or to remove, such coatings, including ultrasonic cleaners, spray jets, mechanical "windshield" wipers, and even arrangements which automatically retract, clean and reinsert the probe. Each of these approaches has distinct disadvantages. Ultrasonic cleaners have difficulty maintaining sufficient energy density at the optic, and do not operate well in viscous fluids. Spray jets are affected by process flows, and require large volumes of solvent. Mechanical approaches introduce unwanted sealing requirements into the process, and may pose safety and/or reliability problems.

SUMMARY OF THE INVENTION

This invention resides in an optical probe with a self-cleaning sampling window, a feature which is particularly useful in on-line process-control environments. The concepts are ideally suited to Raman and fluorescence detection, through the apparatus and methods are not limited in this regard.

In terms of hardware, the apparatus includes a probe body having a window with a surface oriented toward a sample under investigation. A sampling beam carrying wavelengths representative of the sample passes into the probe body through the window for analysis. A conduit, preferably forming part of the probe body, is used to carry a fluid to the surface of the window oriented toward the sample, and a partition proximate to the window is used to direct the fluid across the window as a laminar or turbulent flow.

In a preferred configuration, the partition further includes an aperture through which the sampling wavelengths pass. This partition also permits a portion of the fluid to pass though the aperture to ensure that the sample under investigation does not reach the window. The fluid may be a liquid or gas, depending upon the nature of the sample, and is preferably a solvent to maximize window cleaning. Although the fluid may be discharged without entering into the environment being sampled, the fluid may also be discharged into the sample, depending upon the application, volume of the respective fluid/sample flows, and other such factors.

DETAILED DESCRIPTION OF THE INVENTION

Figure 1:
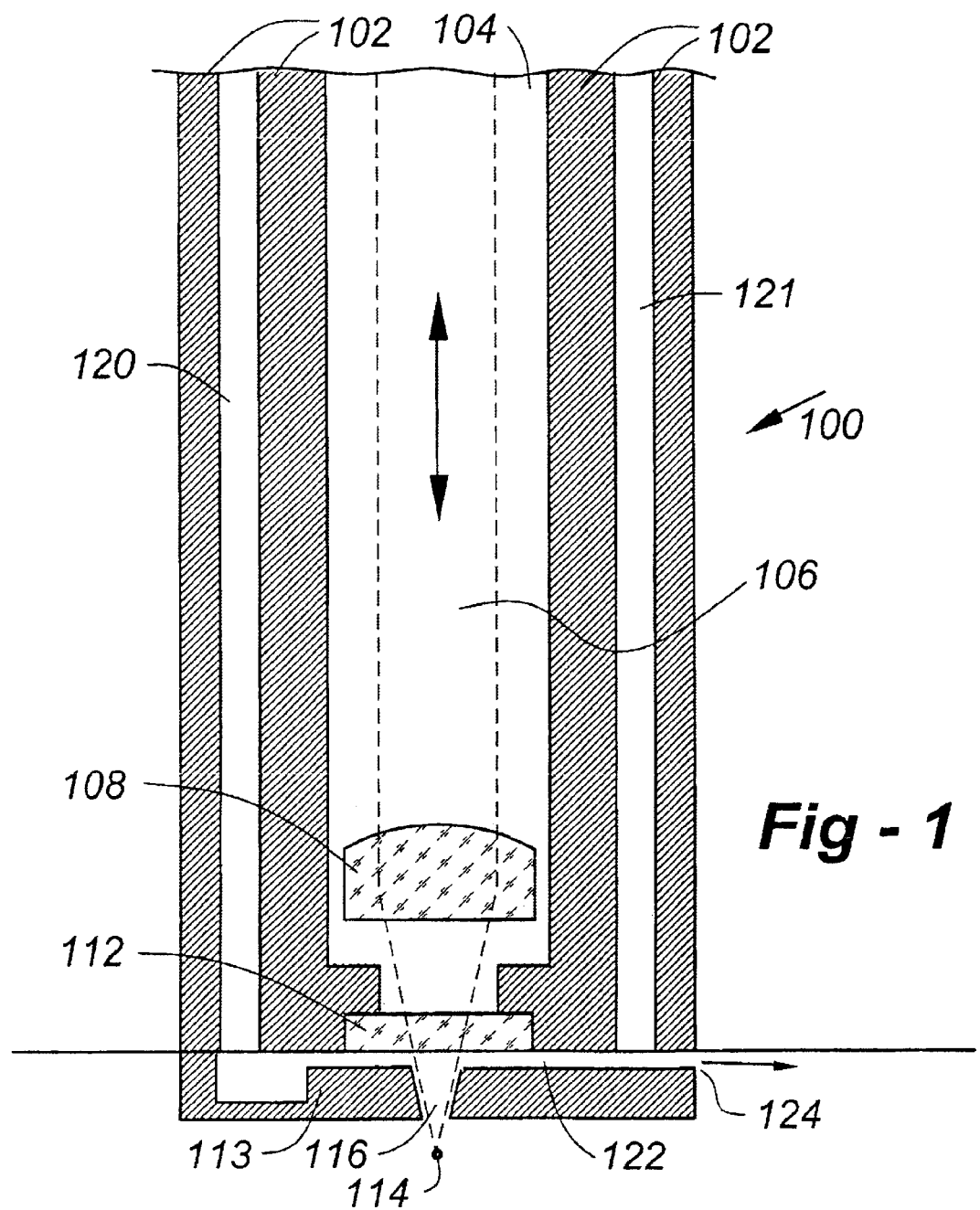
FIG. 1 is a drawing in cross-section illustrating a preferred embodiment of the invention.

Broadly, and in general terms, this invention utilizes a flowing solvent as opposed ato a jet-spray to keep clean a window used in conjunction with a sampling beam of a spectroscopic system. The approach is applicable to any form of optical sampling, including Raman detection, fluorescence, and so forth. In the preferred embodiment, the solvent used for cleaning is supplied as a laminar sheet over and past the surface of the window exposed to the process flow. Alternatively, other "fluids" may be used in lieu of solvents, including gases, particularly if applied in sheet form, depending upon the type of process flow involved.

The invention will be better understood with reference to FIG. 1, which illustrates a preferred embodiment in cross-section generally at 100. Within a probe body 102, there is housed an optical channel 104 containing a sampling beam 106. A sampling lens 106 is used to focus the beam to a localized sampling zone 114 through a sampling port 116. In this example, it is assumed that the beam 106 includes both excitation (i.e., laser) and collected wavelengths in a counter-propagating beam, though the invention is applicable to a collection-only path, assuming no requirement for excitation, or excitation originating from a different direction.

Also contained within the probe body 102 are one or more delivery tubes 120, delivering the cleaning fluid into a gap 122 on the process side of window 112. A partition 113 or other structure is provided to flood a small portion of the window actually used by the sampling beam, as shown, thereby protecting the window from contamination. It is also assumed that the solvent is substantially transparent to the wavelengths being collected through the window, such that the solvent itself will not contaminate or appreciably modify the sample spectra.

The solvent flow may be laminar or turbulent, and may be aspirated through the sample port and entrained through an output port 124 into the solvent flow. This ensures that a representative sample is always available to the sampling zone. Since there is a danger that materials within the process flow may clog the sample port, a second sample delivery tube 121 is positioned "downstream" of the window. Solvent introduced into the tube 121 would serve to increase the back pressure and drive the solvent forceably out the sample port, thereby cleaning the entire sampling area.

It will appreciated to those of skill that the system just described may be operated continuously during data collection, or only on occasion to clean the window in between data collection events.

I claim:

1. An optical probe with a self-cleaning sampling window, comprising:

a probe body having a window with a surface oriented toward a sample under investigation;

a sampling beam of light carrying wavelengths representative of the sample into the probe body through the window for analysis;

a conduit carrying a fluid to the surface of the window oriented toward the sample;

a structure operative to flood the window with the fluid, the structure including an aperture through which the sampling wavelengths pass; and wherein at least a portion of the fluid passes though the aperture to ensure that the sample under investigation does not reach the window.

2. The optical probe of claim 1, wherein the wavelengths are representative of Raman or fluorescence spectra.

3. The optical probe of claim 1, wherein the fluid is a solvent.

4. The optical probe of claim 1, wherein the fluid is a liquid.

5. The optical probe of claim 1, wherein the fluid is a gas.

6. The optical probe of claim 1, wherein the fluid enters into the sample under investigation after flooding the window.

7. An optical probe with a self-leaning sampling window, comprising:

a probe body having a window with a surface oriented toward a sample under investigation;

a sampling beam carrying Raman or fluorescene wavelengths representative of the sample into the probe body through the window for analysis;

a conduit carrying a fluid to the surface of the window oriented toward the sample;

a structure operative to flood the window with the fluid, the structure further including an aperture through which the sampling wavelengths pass; and wherein at least a portion of the fluid pase though the aperture to ensure that the sample under investigation does not reach the window.

8. The optical probe of claim 7, wherein the fluid is a solvent.

9. The optical probe of claim 7, wherein the fluid is a liquid.

10. The optical probe of claim 7, wherein the fluid is a gas.

11. The optical probe of claim 7, wherein the fluid enters into the sample under investigation after flooding the window.

* * * * *